US012734193B2

(12) United States Patent
Tsirikos-Karapanos et al.

(10) Patent No.: US 12,734,193 B2
(45) Date of Patent: Sep. 15, 2026

(54) AMMONIUM CHLORIDE FORMULATION TO SUPPORT HUMAN NATURAL DEFENSE AGAINST VIRUSES

(71) Applicant: Nikolaos Tsirikos-Karapanos, Cleveland, OH (US)

(72) Inventors: Nikolaos Tsirikos-Karapanos, Cleveland, OH (US); Nikolaos Drakoulis, Athens (GR)

(73) Assignee: Nikolaos Tsirikos-Karapanos, Cleveland, OH (US)

( * ) Notice: Subject to any disclaimer, the term of this patent is extended or adjusted under 35 U.S.C. 154(b) by 0 days.

(21) Appl. No.: 17/532,582

(22) Filed: Nov. 22, 2021

(65) Prior Publication Data

US 2022/0160757 A1 May 26, 2022

Related U.S. Application Data

(60) Provisional application No. 63/116,237, filed on Nov. 20, 2020.

(51) Int. Cl.

*A61K 33/20* (2006.01)
*A61K 31/59* (2006.01)
*A61K 47/12* (2006.01)
*A61K 47/38* (2006.01)

(52) U.S. Cl.

CPC .............. *A61K 33/20* (2013.01); *A61K 31/59* (2013.01); *A61K 47/12* (2013.01); *A61K 47/38* (2013.01)

(58) Field of Classification Search

CPC ...................................................... A61K 33/20
See application file for complete search history.

(56) References Cited

U.S. PATENT DOCUMENTS 5,275,828 A 1/1994 Hooper
8,840,934 B2 * 9/2014 Kiassos .................. A61J 1/035 424/455
10,980,756 B1 * 4/2021 Glick .................. A61K 31/135
2002/0198231 A1 12/2002 Nelson
2007/0134166 A1 6/2007 Hunt et al.
2009/0053263 A1 2/2009 Cunningham et al.
2013/0183289 A1 * 7/2013 Gorelik ................ A61K 31/196 604/522
2016/0346320 A1 12/2016 Lang et al.
2017/0128486 A1 * 5/2017 Desbarats ............... A23L 33/16
2018/0214399 A1 8/2018 Spector et al.
2020/0289494 A1 9/2020 McGurk et al.

OTHER PUBLICATIONS

Mizzen et al., Attenuation of Murine Coronavirus Infection by Ammonium Chloride, Virology, 1985 (Year: 1985).*
Baker et al., Repurposing Quaternary Ammonium Compounds as Potential Treatments for COVID-19, Pharmaceutical Research, 2020 (Year: 2020).*
Nuckchady, Hyperpyrexia and metabolic alkalosis in a COVID-19 patient, Journal of Medical Virology, 2020 (First published: Jul. 8, 2020). (Year: 2020).*
Baker, Repurposing Quaternary Ammonium Compounds as Potential Treatments for COVID-19, 2020 (Year: 2020).*
https://www.eastalabamahealth.org/news-and-media/a-look-at-the-three-most-common-types-of-covid-19-tests (Year: 2020).*
Bishop, Examination of Potential Inhibitors of Hepatitis A Virus Uncoating, 1998, Intervirology, vol. 41, p. 261-271. p. 261, summary, p. 262, col. 2, para 1, p. 262, table 1, p. 264, col. 1, para 2, p. 265, col. 1, para 1, p. 2G8. col 1. para 1.
Chen et al. Efficacy of hydroxychloroquine in patients with COVID-19: results of a randomized clinical trial. medRxiv. Apr. 10, 2020 [online], [Retrieved on Mar. 10, 2022], Retrieved from the Internet: <URL: https.ffwww.medrxiv.org/oontont/mBdrxiv/earJy/2020/30/2020.03.22.20040758. full.pdf> p. 6, para 1.
Written Opinion of the International Searching Authority dated Apr. 13, 2022.
Baker, Nancy, et al., "Repurposing Quaternary Ammonium Compounds as Potential Treatments for COVID-19", Pharmaceutical Research, 2020, 37: 104, Springer, https://doi.org/10.1007/s11095-020-02842-8.

* cited by examiner

*Primary Examiner* — Brian-Yong S Kwon
*Assistant Examiner* — Danielle Kim
(74) *Attorney, Agent, or Firm* — Jacob M. Ward; Ward Law Office LLC

(57) ABSTRACT

Formulations and uses thereof are provided for supporting human natural defense against viral infections as well as providing treatment for viral infections susceptible to a lysosomotropic agent. Administration of a lysosomotropic agent, such as ammonium chloride ($NH_4Cl$), can militate against the uncoating of viruses within the lysosome of an infected cell and thereby minimize infection by viruses whose replication cycle relies upon an uncoating step in such a manner.

19 Claims, 6 Drawing Sheets

Figure 1:
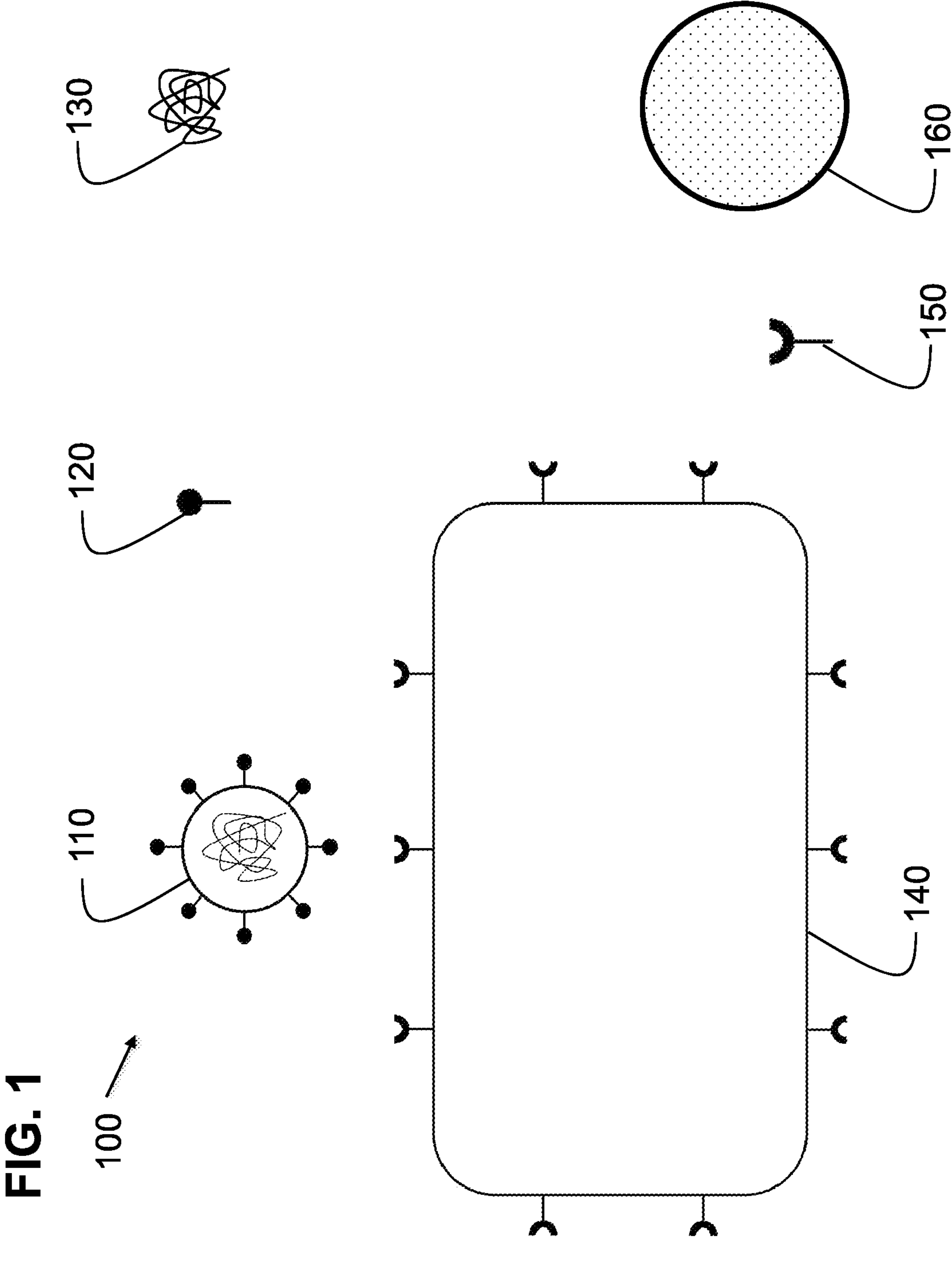

100
110
120
130
140
150
160

200
210
220
230
240
250
260
270
280

Ammonium Chloride
Sodium Croscarmellose
Hydroxypropyl methylcellulose
Magnesium stearate
Microsphere
1
Microsphere Sustained Release Formulation
2
Enteric Coated Softgel or Capsule Filled with Microspheres

FIG. 5

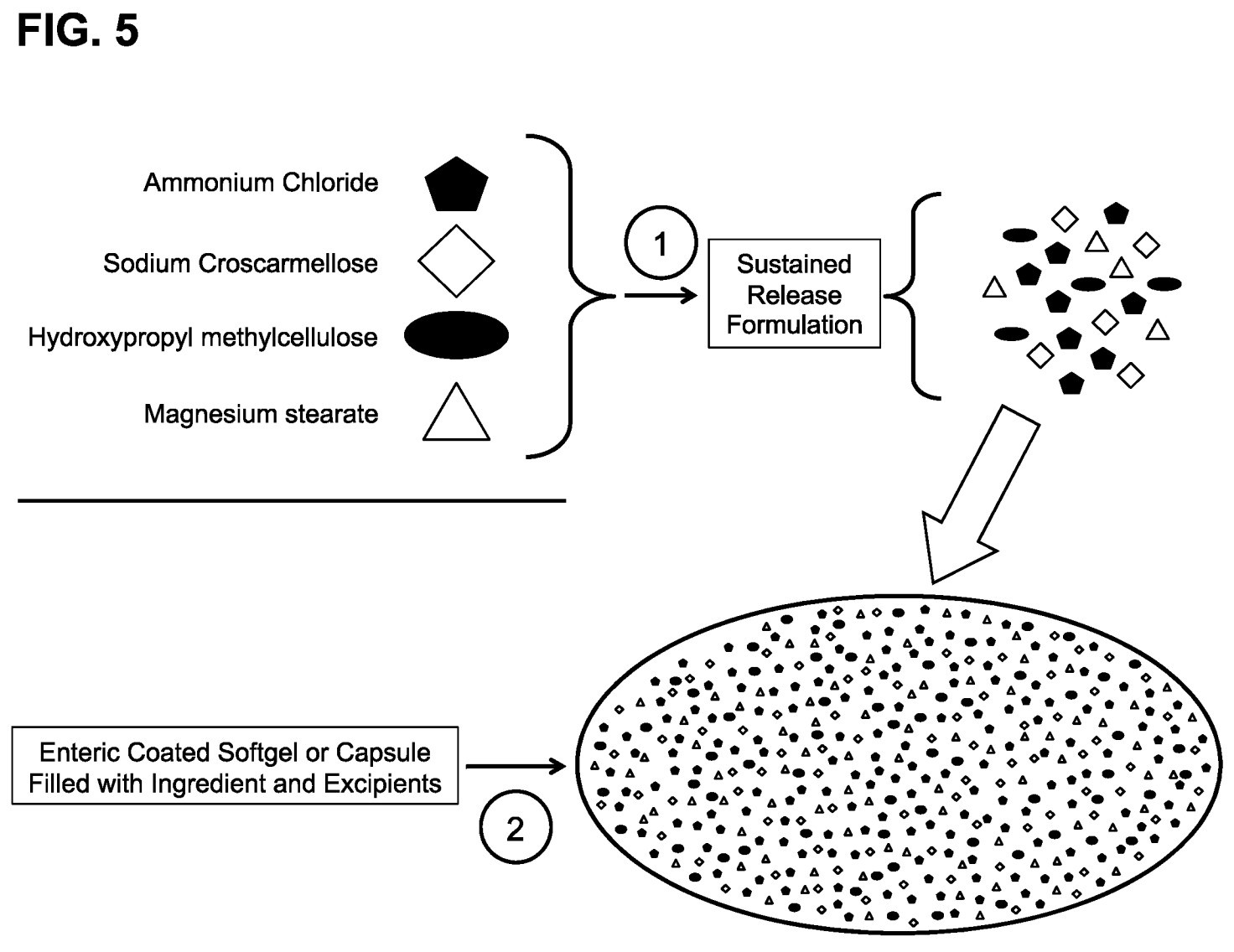

Ammonium Chloride

Sodium Croscarmellose

Hydroxypropyl methylcellulose

Magnesium stearate

1

Sustained Release Formulation

2

Enteric Coated Softgel or Capsule Filled with Ingredient and Excipients

AMMONIUM CHLORIDE FORMULATION TO SUPPORT HUMAN NATURAL DEFENSE AGAINST VIRUSES

CROSS-REFERENCE TO RELATED APPLICATIONS

This application claims the benefit of U.S. Provisional Application No. 63/116,237, filed on Nov. 20, 2020. The entire disclosure of the above application is incorporated herein by reference.

FIELD

The present technology relates to novel dietary supplement and pharmaceutical formulations of a lysosomotropic agent, where dietary supplement formulations of the lysosomotropic agent can be used to support the natural defense of a subject against viral infections, and where pharmaceutical formulations of the lysosomotropic agent can be used to provide treatment for viral infections.

BACKGROUND

This section provides background information related to the present disclosure, which is not necessarily prior art.

Various viruses are responsible for serious diseases in various subjects, including animals and humans, including the Influenza A and Influenza B viruses, the Respiratory Syncytial Virus (SRV), the Syncytial Acute Respiratory Syndrome Coronavirus (SARS-CoV), the SARS-CoV-2 and the Middle East Respiratory Syndrome Virus (MERS). Certain viruses can infect subjects of different species, whereas other viruses can be host species specific.

The first identified strain of SARS-CoV was identified in 2003 in China. SARS-CoV is believed to be an animal virus from an as-yet-uncertain animal reservoir (e.g., bats) that spread to other animal species (e.g., cats) and then infected humans; first, in southern China in 2002. SARS-CoV is primarily transmitted from person-to-person due to virus excretion in respiratory secretions. Twenty-six countries were affected during the SARS epidemic with more than 8,000 cases reported in 2003.

SARS-CoV-2 is the pathogen leading to coronavirus disease (COVID-19). The 2020 COVID-19 pandemic is having a serious global socioeconomic impact. As of November 2020, more than 11,000,000 COVID-19 cases have been confirmed in the U.S. and more than 250,000 people have died from COVID-19 disease. COVID-19 symptoms may appear 2-14 days after the exposure to the SARS-CoV-2 virus. The clinical manifestations of the COVID-19 disease vary. In general, fever, cough, and shortness of breath are common clinical manifestations of the COVID-19 disease accompanied by chills, ageusia (loss of taste), anosmia (loss of smell), muscular aches, headache, sore throat, and gastrointestinal symptoms (vomiting and diarrhea). COVID-19 patients symptoms range from being asymptomatic or having minor respiratory symptoms up to having serious respiratory and general symptoms requiring hospitalization and/or ICU treatment, including endotracheal intubation and respiratory support by a mechanical ventilator. Symptomatic and asymptomatic COVID-19 patients have similar viral load indicating that patients can transmit the virus regardless of the severity of their symptoms. This makes it very difficult to control of the spread of the disease.

There are limited etiological therapies for the COVID-19 disease available, including certain vaccines and antiviral agents, where treatment of COVID-19 patients is sometimes limited to alleviation of symptoms and provision of organ support as needed by the individual patient. Not all patients have access to certain therapies and not all therapies available to date are applicable to certain patients. Accordingly, there is a continuing need for ways to treat COVID-19 patients.

SUMMARY

In concordance with the instant disclosure, the present technology includes articles of manufacture, systems, and processes that relate to supporting human natural defense against viral infections as well as providing treatment for viral infections susceptible to a lysosomotropic agent. Various ways are provided to support natural defenses against viral infections and/or provide treatment of viral infections in a subject, such as a human or animal subject. Administration of a lysosomotropic agent, such as ammonium chloride ($NH_4Cl$), can be used to minimize clinical manifestations of viral infections, including infection by the SARS-CoV-2 virus.

Certain embodiments include methods of militating against a clinical manifestation of infection by a virus in a subject. Such methods can administer a formulation to the subject, where the formulation includes a lysosomotropic agent, the lysosomotropic agent thereby interfering with viral uncoating, providing a viral-static effect, and allowing immunological mechanisms of the subject to produce antibodies against the virus. The lysosomotropic agent can include ammonium chloride and the formulation can be configured in a unit dosage form. The formulation can include an enteric coating configured for oral administration. The lysosomotropic agent can be comprised by microspheres that provide a sustained release of the lysosomotropic agent, where the microspheres are enclosed by the enteric coating.

Certain embodiments include formulations for militating against a clinical manifestation of infection by a virus in a subject. Such formulations can include a lysosomotropic agent, such as ammonium chloride in an amount from about 10 mg to about 2,000 mg. The formulation can be configured in a unit dosage form and can include an enteric coating configured for oral administration. Various excipients can be included in the formulation, such as sodium croscarmellose in an amount from about 10 mg to about 200 mg, hydroxypropyl methylcellulose in an amount from about 10 mg to about 200 mg, and/or magnesium stearate in an amount from about 0.1 mg to about 40 mg. The lysosomotropic agent can be comprised by microspheres that provide a sustained release of the lysosomotropic agent following oral administration, where the microspheres are enclosed by the enteric coating. The formulation can also include vitamin D in an amount from about 1,000 to about 4,000 IU.

The lysosomotropic agent can be used to militate against clinical manifestation of a viral infection in a subject, including infection by the SARS-CoV-2 virus. The lysosomotropic agent can prevent viral uncoating in the subject, thereby resulting in a viral-static effect that can be adequate to provide the necessary time for mounting of natural defense mechanisms in the subject. In particular, the viral-static effect can permit the immune system of the subject enough time to produce a sufficient number of antibodies against the virus to mount an effective immunological response thereto.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes and are not intended to limit the scope of the present disclosure.

FIG. 1 depicts schematic representations of various SARS-CoV-2 virus and host cell (e.g., animal or human cell) components referenced in the present disclosure, identified as follows: (A) SARS-CoV-2 virus, (B) SARS-CoV-2 surface spike protein ("S protein"), (C) SARS-CoV-2 genetic material (RNA), host cell (human cell), (E) Angiotensin Converting Enzyme II ("ACE-2") receptor, (F) lysosome of the host cell.

Figure 2:
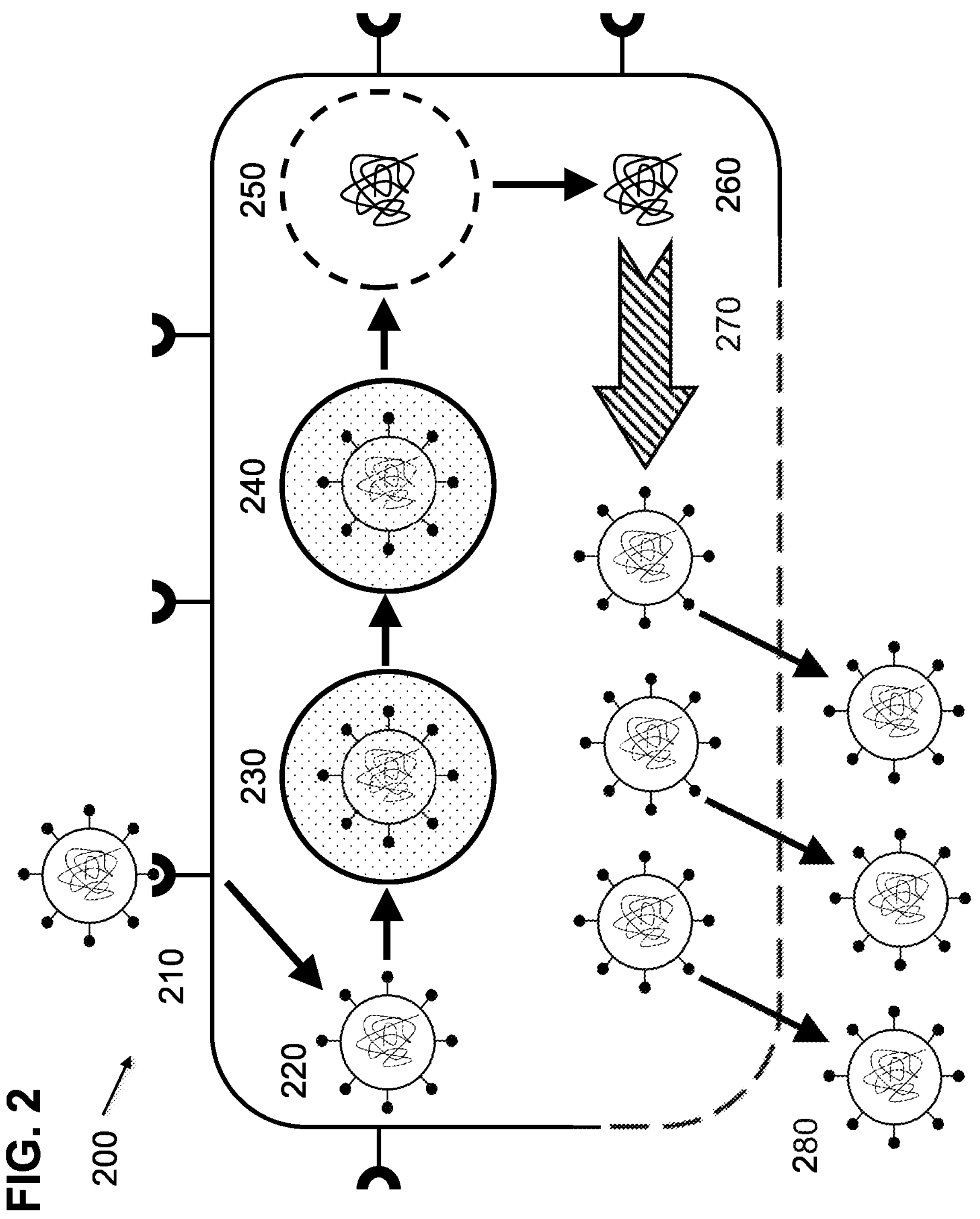

FIG. 2 depicts the natural course of the SARS-CoV-2 virus infection of a host cell, with reference to the schematic representations of the components identified in FIG. 1.

Figure 3:
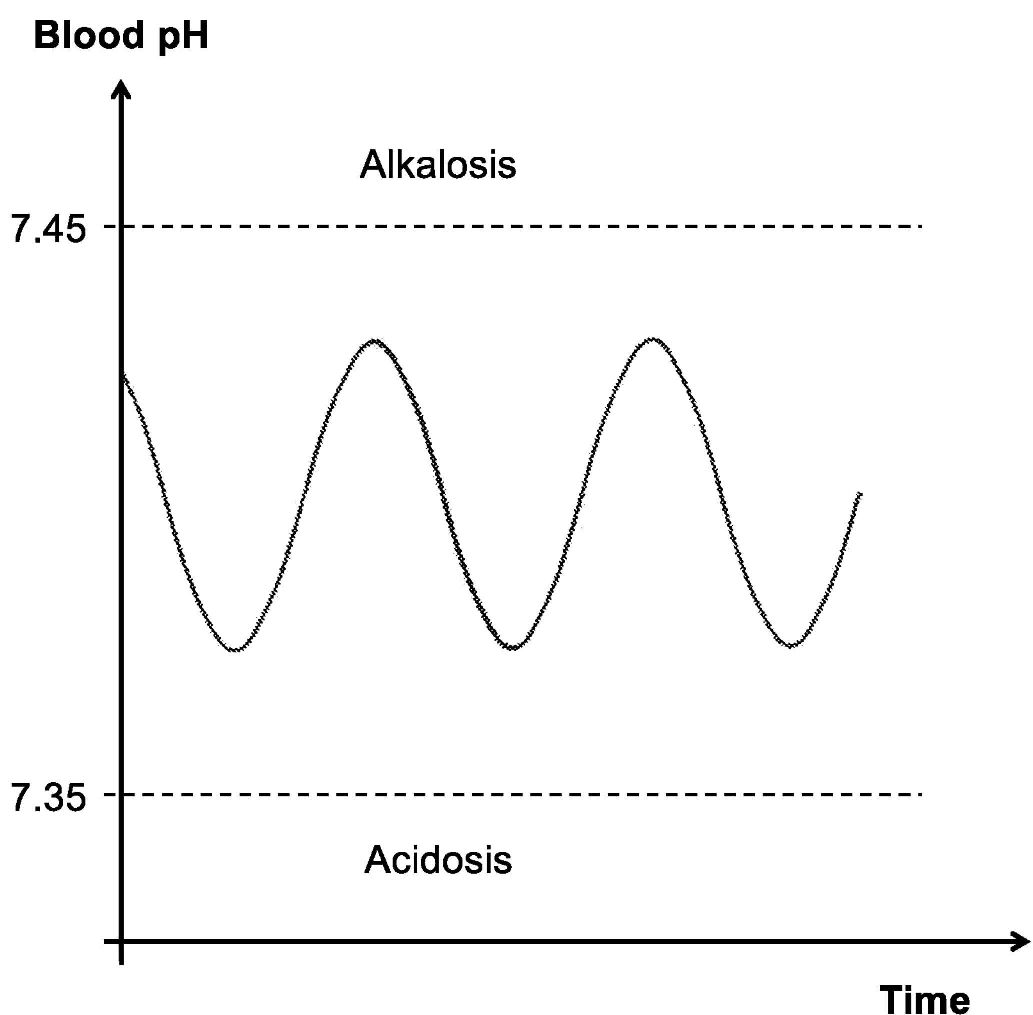

FIG. 3 graphically depicts physiologic or acceptable blood pH variation overtime.

Figure 4:
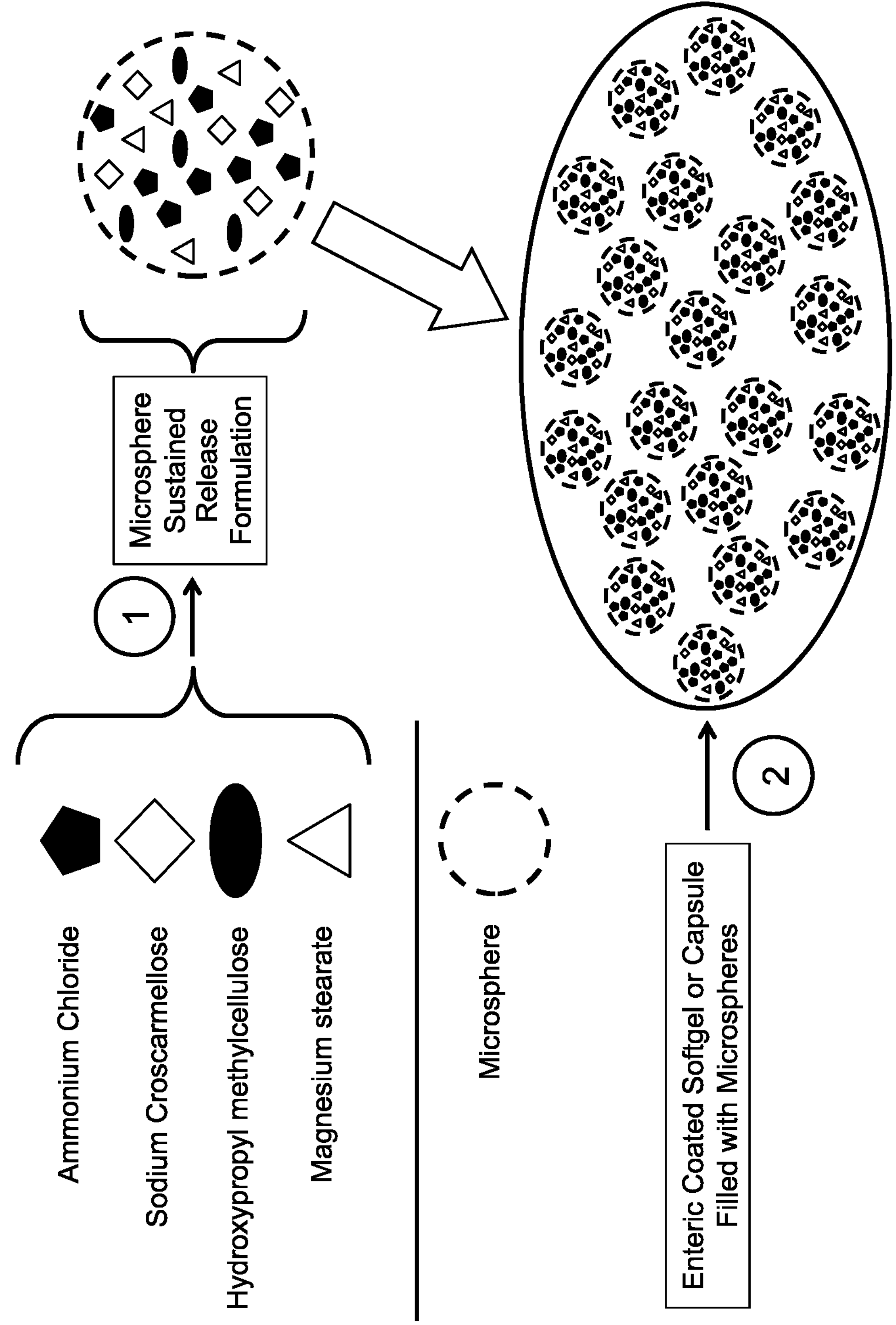

FIG. 4 depicts schematic representations of components used in the preparation of an ammonium chloride formulation according to an embodiment of the present technology, where the lysosomotropic agent $NH_4Cl$ and excipients are mixed and formulated in microspheres that are further inserted into an enteric coated softgel or into an enteric coated capsule capable of sustained release of the lysosomotropic agent after the enteric coated softgel or the enteric coated capsule dissolves at the small bowel.

FIG. 5 depicts schematic representations of components used in the preparation of an ammonium chloride formulation according to an embodiment of the present technology, where the lysosomotropic agent $NH_4Cl$ and the excipients are mixed and formulated in a sustained release enteric coated softgel or enteric coated capsule formulation capable of sustained release of the lysosomotropic agent after the enteric coated softgel or the enteric coated capsule dissolves at the small bowel.

Figure 6:
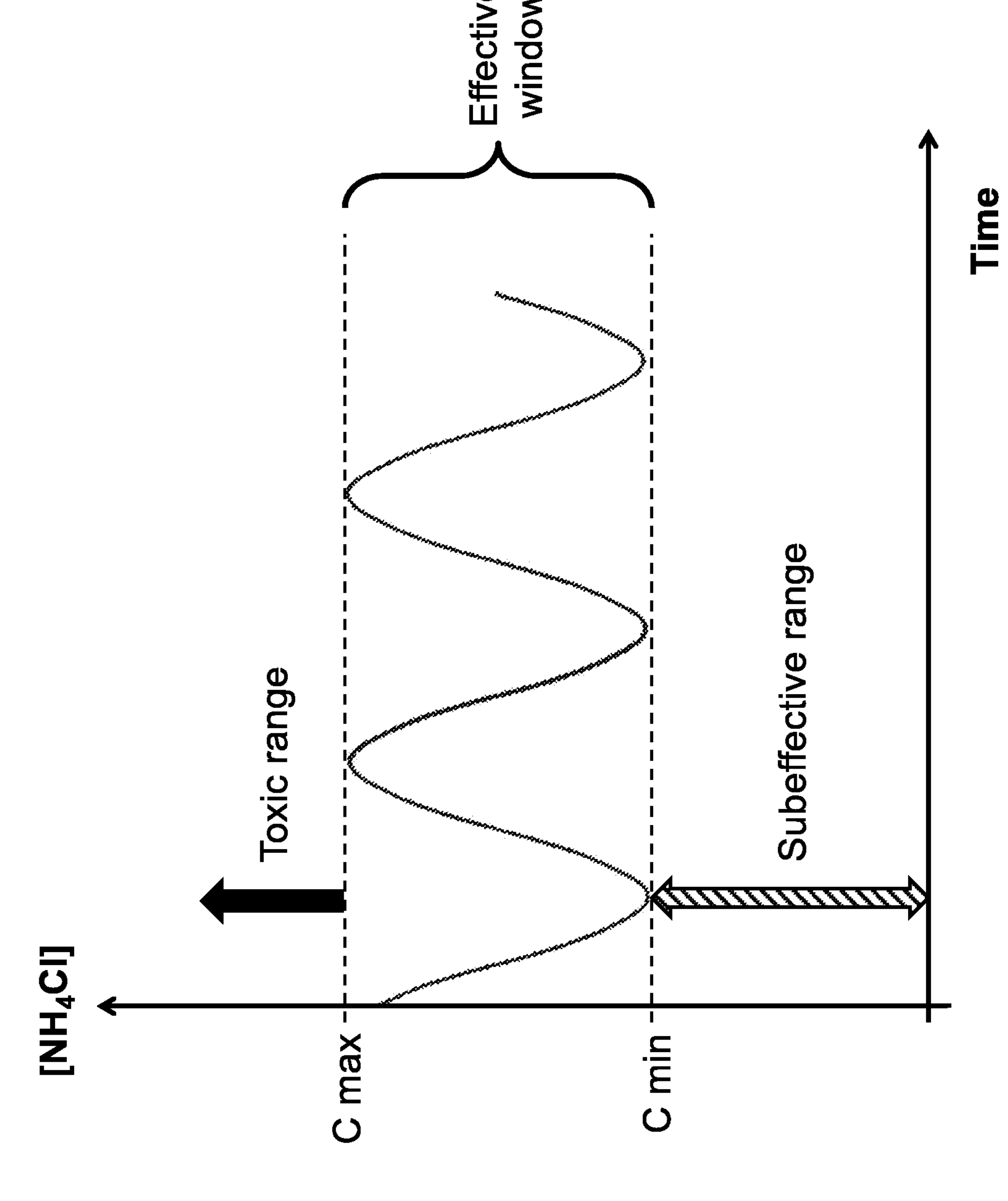

FIG. 6 depicts a schematic representation of the blood concentration of $NH_4Cl$ after its release from the sustained release formulation and its absorption, where Cmin represents a minimum effective $NH_4Cl$ blood concentration, Cmax represents a minimum toxic $NH_4Cl$ blood concentration, and [Cmax−Cmin] represents an effective $NH_4Cl$ blood concentration window.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. Regarding methods disclosed, the order of the steps presented is exemplary in nature, and thus, the order of the steps can be different in various embodiments, including where certain steps can be simultaneously performed. "A" and "an" as used herein indicate "at least one" of the item is present; a plurality of such items may be present, when possible. Except where otherwise expressly indicated, all numerical quantities in this description are to be understood as modified by the word "about" and all geometric and spatial descriptors are to be understood as modified by the word "substantially" in describing the broadest scope of the technology. "About" when applied to numerical values indicates that the calculation or the measurement allows some slight imprecision in the value (with some approach to exactness in the value; approximately or reasonably close to the value; nearly). If, for some reason, the imprecision provided by "about" and/or "substantially" is not otherwise understood in the art with this ordinary meaning, then "about" and/or "substantially" as used herein indicates at least variations that may arise from ordinary methods of measuring or using such parameters.

All documents, including patents, patent applications, and scientific literature cited in this detailed description are incorporated herein by reference, unless otherwise expressly indicated. Where any conflict or ambiguity may exist between a document incorporated by reference and this detailed description, the present detailed description controls.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components, or process steps, the present technology also specifically includes embodiments consisting of, or consisting essentially of, such materials, components, or process steps excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein.

As referred to herein, all compositional percentages are by weight of the total composition, unless otherwise specified. Disclosures of ranges are, unless specified otherwise, inclusive of endpoints and include all distinct values and further divided ranges within the entire range. Thus, for example, a range of "from A to B" or "from about A to about B" is inclusive of A and of B. Disclosure of values and ranges of values for specific parameters (such as amounts, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, 3-9, and so on.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The present technology includes ways of militating against a clinical manifestation of infection by a virus in a subject, including infection by the SARS-CoV-2 virus. Methods are provided that include administering a formulation to the subject, where the formulation includes a lysosomotropic agent. The lysosomotropic agent can therefore interfere with viral uncoating, provide a viral-static effect, and allow immunological mechanisms of the subject to produce antibodies against the virus.

The administered formulation can include various aspects. The lysosomotropic agent can include ammonium chloride and the formulation can be configured in a unit dosage form. Certain embodiments include where the formulation has an enteric coating configured for oral administration. The enteric coating can be configured to release formulation components in the gastrointestinal tract after the stomach, for example, in the duodenum or upper tract of the intestine. The lysosomotropic agent can be present in or take the form of microspheres that provide a sustained release of the lysosomotropic agent. The microspheres themselves can be enclosed by the enteric coating. For example, the enteric coating can take the form of a softgel or capsule that can enclose a quantity of microspheres. The formulation can include one or more excipients, such as sodium croscarmellose, hydroxypropyl methylcellulose, and/or magnesium stearate. Embodiments of the formulation can further include vitamin D.

The methods of militating against a clinical manifestation of infection by a virus in a subject can further include various aspects. Embodiments include adjusting the administering of the formulation to the subject so that the subject is not exhibiting alkalosis and not exhibiting acidosis. For example, certain methods can include measuring a blood pH of the subject and adjusting the administering of the formulation to the subject until the blood pH of the subject is between about 7.35 and about 7.45. It is further possible to continue the administration of the formulation to the subject until an antibody to the virus is detected in the subject. It is also further possible to continue the administration of the formulation to the subject until the virus cannot be detected in the subject; for example, where the subject exhibits a negative viral test. The negative viral test can be based upon a polymerase chain reaction (PCR) test or reverse-transcription polymerase chain reaction (RT-PCR) test for viral genetic material and/or an antibody-based test for a viral antigen.

Certain embodiments of the present technology can utilize formulations with the following aspects. The lysosomotropic agent can include ammonium chloride in an amount from about 10 mg to about 2,000 mg per day. The formulation can further includes: sodium croscarmellose in an amount from about 10 mg to about 200 mg a day; hydroxypropyl methylcellulose in an amount from about 10 mg to about 200 mg a day; and/or magnesium stearate in an amount from about 0.1 mg to about 40 mg a day. The formulation can be configured in a unit dosage form and can include an enteric coating configured for oral administration. The ammonium chloride, the sodium croscarmellose, the hydroxypropyl methylcellulose, and the magnesium stearate can be comprised by microspheres, where the microspheres are enclosed by the enteric coating and provide a sustained release of the ammonium chloride.

Certain embodiments of the present technology include formulations configured for external topical use and administering the formulation to the subject can include application of the formulation to subject's skin. The formulation can be configured for sustained release of the lysosomotropic agent to the subject's skin.

The present technology further provides formulations for militating against a clinical manifestation of infection by a virus in a subject. Such formulations can have a lysosomotropic agent including ammonium chloride in an amount from about 10 mg to about 2,000 mg. The formulation can be configured in a unit dosage form, such as a solid unit dosage form, and can include an enteric coating configured for oral administration. As described for uses of the formulation, the formulation can further include various excipients, such as sodium croscarmellose in an amount from about 10 mg to about 200 mg per day, hydroxypropyl methylcellulose in an amount from about 10 mg to about 200 mg per day, and/or magnesium stearate in an amount from about 0.1 mg to about 40 mg per day. The lysosomotropic agent can be enclosed by an enteric coating that is configured for sustained release of the lysosomotropic agent. The lysosomotropic agent can be comprised by microspheres to provide a sustained release of the lysosomotropic agent, where an amount of microspheres can be enclosed by the enteric coating. Certain formulations can further include vitamin D in an amount from about 1,000 to about 4,000 IU per day.

The present technology takes advantage of aspects of the replication cycle of certain viruses, including SARS-CoV-2. Viruses cannot replicate themselves; they need to insert into a host cell in order to replicate. Once a virus enters into the host cell, the virus needs to release its genetic material (e.g., RNA for SARS-CoV-2) into the host cell cytoplasm and use the host cell "machinery" to produce the elements needed for the replication of the virus. This results in the intracellular production of several viruses that, after the host cell's death, are released and are ready to infect other healthy host cells.

With respect to SARS-CoV-2, particular features of the virus operate at certain points in the replication cycle. The SARS-CoV-2 virus surface spike protein ("S protein") has a high affinity for the ACE-2 receptor of various host cells (e.g., human host cells). Human cells with ACE-2 receptors on their surface, for example, include Type-II alveolar cells in the lung, as well as cells in several extra-pulmonary tissues, including cells in the heart, kidneys, and intestines. The genetic material of the SARS-CoV-2 virus is RNA. For the SARS-CoV-2 virus to replicate, it needs to release its RNA into the cytoplasm of a host cell.

FIG. 1 shows schematic representations of components 100 of the SARS-CoV-2 virus and the host cell (e.g., animal or human cell), including the following: SARS-CoV-2 virus 110, SARS-CoV-2 surface spike protein ("S protein") 120, SARS-CoV-2 genetic material (RNA) 130, host cell (human cell) 140, Angiotensin Converting Enzyme II ("ACE-2") receptor 150, lysosome of the host cell 160. The general representations of these components are used in the viral infection steps shown in FIG. 2. It should be understood that the components depicted in FIGS. 1-2 and the steps shown in FIG. 2 are for general reference of certain aspects and events in viral infection and replication, and are not intended to be complete or rigidly define such. Other viral and host components may be involved and stages of viral infection and replication are not necessarily discrete or limited to the depicted features.

The natural course of the SARS-CoV-2 virus infection of a host cell and SARS-CoV-2 virus replication generally includes the following aspects. Once the SARS-CoV-2 virus infects a human, for example by entering into the human respiratory system, the following general sequence of steps occurs, as illustrated by the steps shown at 200 in FIG. 2. At step 210, the SARS-CoV-2 virus S protein "anchors" at the ACE-2 receptor of the host cell. At step 220, the SARS-CoV-2 virus enters into the host cell cytoplasm via a receptor-mediated endocytosis mechanism. At step 230, once inside the host cell cytoplasm, the SARS-CoV-2 virus enters into a host cell's lysosome. The normal lysosome pH is acidic ranging from around 4.5 to 5.0. At step 240, inside the host cell's lysosome and under the influence of lysosomal degenerative enzymes (e.g., lysosomal hydrolases) the SARS-CoV-2 viral membrane breaks. This process, known as "uncoating," is pH dependent. Lysosomal hydrolases causing the SARS-CoV-2 virus uncoating include enzymes active only at the acidic lysosomal pH (4.5-5.0), which become inactive at less acidic pH and in neutral pH. In order to maintain an acidic lysosomal state within the range of pH 4.5 to 5.0, lysosomal membrane proteins pump protons (i.e., $H^+$ ions) from the cytoplasm of the cell into the lysosome. The cytoplasm pH is slightly alkaline (e.g., about pH 7.2). At step 250, the SARS-CoV-2 virus uncoating results in the SARS-CoV-2 RNA being released into the lysosome. At step 260, the SARS-CoV-2 RNA is released into the cytoplasm. At step 270, once in the cytoplasm, the SARS-CoV-2 RNA directs the host cell machinery to start translating the SARS-CoV-2 RNA into viral proteins, including an RNA dependent RNA polymerase that replicates the viral RNA, resulting in SARS-CoV-2 viral replication. At step 280, completion of the intracellular SARS-CoV-2 viral replication is followed by host cell death and release of newly assembled SARS-CoV-2 viruses that are now ready to infect other host cells. Post human infection, the process of SARS-CoV-2 replication can be very fast, and the depicted steps are repeated in high speed, where the virus can infect and subsequently kill a very large number of host cells.

There are various aspects of host defense that relate to viral infection. By the moment that the SARS-CoV-2 virus enters the human body, the natural human defense mechanism of antibody formation against the SARS-CoV-2 virus is triggered and specific anti-SARS-CoV-2 virus antibodies begin to be produced. Unfortunately, this natural defense mechanism may be inadequate to protect the host, as the process to produce specific anti-SARS-CoV-2 antibodies in an amount effective against the virus may be significantly slower than the SARS-CoV-2 virus replication rate.

The present disclosure provides a lysosomotropic agent, such as ammonium chloride ($NH_4Cl$), in certain formulations, such as novel dietary supplements and pharmaceutical formulations, that cause an increase of lysosomal pH in the cells of a subject and thus result in blocking the uncoating step of the SARS-CoV-2 virus. Failure to uncoat the SARS-CoV-2 virus, or even pausing or interruption of the uncoating process, as described above and shown in FIG. 2, due to an increased lysosomal pH (i.e., less acidic) can have a viral-static effect. The viral-static effect can significantly delay the SARS-CoV-2 viral replication rate and allow sufficient time for adequate anti-SARS-CoV-2 antibodies to be produced by the infected subject to effectively fight against the SARS-CoV-2 virus infection. The viral-static effect of the lysosomotropic agent alone or in combination with other therapeutic approaches can significantly minimize the clinical manifestations of the COVID-19 disease and reduce the need for hospitalization, ICU treatment, and/or the need for endotracheal intubation and mechanical ventilation. Various formulations including the lysosomotropic agent and various treatment modalities are provided by the present technology.

In certain embodiments, the lysosomotropic agent includes ammonium chloride ($NH_4Cl$), which is a water-soluble salt. Ammonium chloride is a lysosomotropic agent that can act at the lysosome to increase the lysosomal pH by blocking the lysosome membrane proteins pumping protons ($H^+$ ions) from the cytoplasm into the lysosome. Christian De Duve introduced the term "lysosomotropism" in 1974 to describe substances that act selectively at the lysosome ("lysosomotropic" substances). From a regulatory point of view, ammonium chloride is designated as having a Generally Recognized As Safe status (GRAS status) from the U.S. Food & Drug Administration (see 21 CFR § 184.1138) and can be lawfully used in various formulations, including dietary supplements and in pharmaceutical formulations.

Ammonium chloride can further function as excipient in various formulations, including cough and cold medications, and can act as an expectorant to help clear lung secretions. Intravenous ("IV") administration of ammonium chloride can be used for electrolyte replenishment (mainly hypochloremia) and in the treatment of alkalosis. Ammonium chloride is contraindicated in patients with severe impairment of renal or liver function. Rapid IV ammonium chloride administration or ammonium chloride overdose can result in serious metabolic acidosis, disorientation, confusion, and coma. If administered by mouth, ammonium chloride can cause upset stomach.

Where the lysosomotropic agent includes ammonium chloride, the ammonium chloride can alter the pH at various portions of the subject to which it is administered. The blood of the subject, in particular, is typically physiologically regulated. The physiologic pH range of the blood is fairly narrow and is maintained between 7.35-7.45 by various physiological complex homeostatic mechanisms, as graphically depicted in FIG. 3. Physiologic pH of the blood is bounded by an overly alkaline state (alkalosis) and an overly acidic state (acidosis). Alkalosis is the pathologic condition of blood pH being higher than 7.45 and can be the result of either an excess production of bicarbonate in the blood (metabolic alkalosis) or by decreased carbon dioxide levels in the blood (respiratory alkalosis). Alkalosis can cause various symptoms including confusion, nausea, vomiting, muscular twitching, and muscular spasms, which may need to be treated. Acidosis is the pathologic condition of blood pH being lower than 7.35 and can be the result of either an overproduction of an acid in the blood (metabolic acidosis), or by increased carbon dioxide levels in the blood resulting from compromised lung function or by depressed breathing or both (respiratory acidosis). Acidosis can cause various symptoms including confusion, headache, tachypnea (rapid breathing), and tachycardia (increased heart rate), which may need to be treated.

The present novel lysosomotropic agent formulations (incl. ammonium chloride) provided by the present disclosure can be formulated in certain ways to fulfill the following requirements. First, the formulation can be configured to be orally administered. Second, the formulation can be configured to mitigate the risk of gastric side effects (upset stomach). Examples include where the lysosomotropic agent is coated by or packaged within an enteric coating or capsule, such as through use of an enteric coated softgel or capsule. Fourth, the formulation can be configured to mitigate the risk of unwanted blood pH variation outside of the 7.35-7.45 range by having a minimal ammonium chloride concentration variance in the blood and thus mitigate the risk of metabolic acidosis. This can be achieved by configuring the formulation to provide a sustained release of ammonium chloride in the duodenum/small intestine. Fifth, the formulation can result in increased lysosomal pH of the subject's cells and prohibit viral uncoating in lysosomes thereof, including uncoating of the SARS-CoV-2 virus, for example as shown in FIG. 2. It should be noted that the elevation of lysosomal pH by the formulation can be transient and occurs in response to the ammonium chloride administration. Once the administration and/or sustained release of ammonium chloride ends, the lysosomal pH can go back to the normal acidic state. The elevation of the lysosomal pH by the formulation is therefore only temporary and can be controlled by the administration and sustained release of the formulation.

The formulation can be configured as an oral unit dosage form with an enteric coating in order to release the lysosomotropic agent after the stomach, for example, in the upper tract of the intestine. The enteric-coated formulation can provide a sustained release dosage form. Unit dosage form examples including tablets, mini-tablets, pellets and granules or microspheres, usually filled into capsule shells. Enteric coatings can function by presenting a surface that is stable at the acidic pH found in the stomach, but which can break down at a higher pH (e.g., more alkaline pH). For example, the enteric coating will not dissolve in the gastric acids of the stomach (e.g., pH ~3), but will dissolve in the alkaline (pH 7-9) environment present in the small intestine. By preventing dissolution in the stomach, the enteric coating can also protect gastric mucosa from any irritating effects of one or more components of the formulation itself. When the formulation reaches the neutral or alkaline environment of the intestine, the coating can dissolve and components therein are available for absorption into the bloodstream.

There are various ways to make enteric formulations. Enteric coatings can include one or more fatty acids, waxes, shellac, polymers, and/or plant fibers, as known in the art. Certain materials that can be used to successfully formulate enteric coatings or enteric capsules include one or more of methyl acrylate-methacrylic acid copolymers, cellulose acetate phthalate, cellulose acetate succinate, hydroxypropyl methyl cellulose phthalate, hydroxypropyl methyl cellulose acetate succinate (hypromellose acetate succinate), polyvinyl acetate phthalate, methyl methacrylate-methacrylic acid copolymers, shellac, cellulose acetate trimellitate, sodium alginate, and zein. For example, an enteric coating aqueous solution (ethylcellulose, medium chain triglycerides [coconut], oleic acid, sodium alginate, stearic acid) can be used to form coated softgels.

There are various ways to make sustained release formulations. Such sustained release dosage forms include dosage forms configured to release liberate or liberate the lysosomotropic agent at a predetermined rate in order to maintain a constant concentration for a specific period of time with minimum side effects; e.g., deviation outside of a desired blood pH window. This can be achieved through a variety of formulations, including liposomes and drug-polymer conjugates (e.g., hydrogels). Sustained or modified-release dosages can permit the lysosomotropic agent to dissolve over time in order to be released slower and steadier into the bloodstream. A further advantage is that the sustained release formulation can be administered at less frequent intervals than immediate-release formulations of the same drug. The sustained release nature of the formulation can particularly advantageous for oral dose formulations. Timed release has several distinct variants such as sustained release where prolonged release is intended, pulse release, delayed release (e.g., to target different regions of the GI tract) etc. Sustained release not only it prolongs action of the lysosomotropic agent, but can maintain drug levels within the desired therapeutic window to avoid potentially hazardous peaks in drug concentration following ingestion or injection, to thereby maximize therapeutic efficiency.

One particular sustained release means that can be employed in the present formulations includes micro-encapsulation. Use of microspheres in formulation of the lysosomotropic agent can provide a predetermined dissolution profile. Microspheres can be used with enteric coatings or capsules, or the microspheres themselves can incorporate enteric coatings. In particular, the lysosomotropic agent can be coated around an inert core and layering with one or more insoluble substances to form microspheres, which can allow for consistent and replicable dissolution rates in a convenient format that can be mixed and matched with other components and/or pharmaceutical ingredients. It is further possible to make enteric capsules containing more than one type of microsphere, where at least some of the microspheres include the lysosomotropic agent.

In certain embodiments, formulations provided by the present technology include a lysosomotropic agent as ammonium chloride, where the ammonium chloride is in the form of an enteric coated (gastro protective) softgel or capsule filled with microspheres including the components shown in FIG. 4, or with a mixture of the components shown in FIG. 5 not packaged as microspheres. As shown in FIGS. 4-5, the lysomotropic agent as ammonium chloride can be formulated with excipients including sodium croscarmellose, hydroxypropyl methylcellulose, and magnesium stearate. Various unit dosage formulations can be made, including various oral unit dosage formulations. Regulatory status and function of the respective components are summarized in following table.

| # | Component | Quantity | Regulatory Status | Function |
|---|---|---|---|---|
| 1 | $NH_4Cl$ | 10-1,000 mg | GRAS | active ingredient, prohibits viral uncoating and release of viral RNA |
| 2 | sodium croscarmellose | 10-100 mg | GRAS | excipients used for the sustained |
| 3 | hydroxypropyl methylcellulose | 10-100 mg | GRAS | release of $NH_4Cl$ |
| 4 | magnesium stearate | 0.1-20 mg | GRAS | |
| 5 | microspheres | 10-1000 per softgel or capsule | n/a | sustained release of $NH_4Cl$ |
| 6 | enteric coated softgel or capsule | 1-2/day | n/a | mitigation of gastric side effects of $NH_4Cl$ |

All ingredients of the ammonium chloride formulations of the present technology accordingly have GRAS status and can be used as ingredients/excipients in various oral dosage formulations, including formulations as dietary supplements and pharmaceutical formulations.

With reference now to FIG. 6, a graphical representation of blood concentration of ammonium chloride is shown following absorption from a sustained release formulation, where Cmin represents a minimum effective ammonium chloride blood concentration, Cmax represents a minimum toxic ammonium chloride blood concentration, and [Cmax−Cmin] represents an effective ammonium chloride blood concentration window.

In further embodiments of formulations of the lysosomotropic agent, vitamin D can be included in amounts of 1,000-4,000 International Units ("IU") per enteric coated softgel or capsule. Vitamin D can boost a subject's immune system and reduce inflammation, each of which can operate in conjunction with the lysosomotropic agent to militate against the effects of viral infection. Deficiency in vitamin D can also compound issues related to blood clots, where SARS-CoV-2 virus infection can result blood clots that can present serious issues in the subject's brain, heart, and lungs, for example. Formulations of the lysosomotropic agent can therefore include vitamin D to minimize such effects during and after administration.

The present technology further contemplates intravenous (IV) administration of formulations presented herein. Compared toper os (PO; i.e. oral) IV administration of ammonium chloride can have two major advantages. First, IV administration of ammonium chloride bypasses the stomach, and hence gastric side effects (e.g., upset stomach) related to PO administration of ammonium chloride are avoided. Second, the rate of IV administration of ammonium chloride can be easily adjusted, controlled, and monitored in order to avoid issues resulting from excessive administration of ammonium chloride, which can lead to toxic symptoms, including metabolic acidosis, hypokalemia, hypocalcemia, and hyperventilation, while maintaining the desired therapeutic effect.

The PO administration of ammonium chloride as a lysosomotropic agent must be done in such a way to also avoid the aforementioned side effects. In order to avoid the gastric side effects, the ammonium chloride can be formulated as a gastroprotective formulation (e.g., having an enteric coating) and be released from its gastroprotective formulation only after passing the stomach. The rate of ammonium chloride release from its gastroprotective formulation in the gut should be substantially constant in order to mimic the IV administration pharmacokinetic profile. The rate of ammonium chloride release from its gastroprotective formulation can be related to various specific formulation characteristics of its gastroprotective formulation including: (1) the quantity of ammonium chloride within its gastroprotective formulation; (2) the type of the excipients that are used in the gastroprotective formulation; (3) the quantity of each excipient used in the gastroprotective formulation; (4) the rate of ammonium chloride release from its gastroprotective formulation can be directly related with the rate of ammonium chloride absorption in the gut and the resulting ammonium chloride blood concentration.

To quantify the rate of ammonium chloride release from its gastroprotective formulation in vitro, it is possible to create various candidate gastroprotective ammonium chloride formulations with various quantities of ammonium chloride and one or more excipients. For each ammonium chloride candidate gastroprotective formulation, an in vitro dissolution study can be performed and a dissolution profile of ammonium chloride concentration over time can be plotted. One goal of such dissolution studies can be to establish an In-Vitro In-Vivo Correlation (IVIVC) as a way to assess the safety and efficacy of the ammonium chloride gastroprotective formulation. It is noted that dissolution methodology is established and well known, and one skilled in the art can readily ascertain a dissolution profile of ammonium chloride concentration over time and establish an IVIVC for various formulations, as presented herein. The U.S. Pharmacopeial Convention has further established certain dissolution measurement standard, where a specific Monograph exists for dissolution, USP <711>. Accordingly, it is possible to perform dissolution studies using the standards established by USP <711>, available at: [www.usp.org/sites/default/files/usp/document/harmonization/gen-method/stage_6_monograph_25_feb_2011.pdf]. Results of the gastroprotective, sustained release ammonium chloride dissolution studies can demonstrate the safety and efficacy of a respective formulation, as provided herein, and cam show that the ammonium chloride release from the formulation and the resulting ammonium chloride absorption in the gut and overall pharmacokinetic profile can mimic the IV ammonium chloride administration pharmacokinetic profile.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms, and that neither should be construed to limit the scope of the disclosure. In some example embodiments, well-known processes, well-known device structures, and well-known technologies are not described in detail. Equivalent changes, modifications and variations of some embodiments, materials, compositions and methods can be made within the scope of the present technology, with substantially similar results.

What is claimed is:

1. A method of treating a clinical manifestation of infection by a virus in a subject in need thereof, the method comprising:

administering a formulation to the subject, the formulation including a lysosomotropic agent, wherein the lysosomotropic agent includes ammonium chloride, whereby the lysosomotropic agent interferes with viral uncoating, provides a viral-static effect, and allows immunological mechanisms of the subject to produce antibodies against the virus, wherein the virus includes SARS-CoV-2 virus;

monitoring the subject for at least one of alkalosis and acidosis, wherein the monitoring includes measuring a blood pH of the subject;

selectively adjusting the administering of the formulation to the subject based on the monitoring so that the subject is not exhibiting alkalosis and is not exhibiting acidosis, wherein the selectively adjusting includes adjusting the administering of the formulation to the subject until the blood pH of the subject is between about 7.35 and about 7.45; and continuing the administration of the formulation to the subject until an antibody to the virus is detected in the subject, wherein:

the formulation includes an enteric coating configured for oral administration; or the formulation is configured for sustained release of the lysosomotropic agent to the subject's skin.

2. The method according to claim 1, wherein the formulation is configured in a unit dosage form, the formulation includes the enteric coating, and the formulation is configured as one of a softgel and a capsule.

3. The method according to claim 1, wherein the lysosomotropic agent is comprised by microspheres providing a sustained release of the lysosomotropic agent, the microspheres enclosed by the enteric coating.

4. The method according to claim 1, wherein the formulation includes an excipient selected from a group consisting of sodium croscarmellose, hydroxypropyl methylcellulose, magnesium stearate, and combinations thereof.

5. The method according to claim 1, further comprising continuing the administration of the formulation to the subject until the virus cannot be detected in the subject.

6. The method according to claim 1, wherein the formulation further comprises vitamin D in an amount from about 1,000 to about 4,000 IU a day.

7. The method according to claim 1, wherein:

the lysosomotropic agent includes ammonium chloride in an amount from about 10 mg to about 2,000 mg per day; and the formulation further includes:

sodium croscarmellose in an amount from about 10 mg to about 200 mg a day;

hydroxypropyl methylcellulose in an amount from about 10 mg to about 200 mg a day; and magnesium stearate in an amount from about 0.1 mg to about 40 mg a day;

wherein the formulation is configured in a unit dosage form and includes the enteric coating configured for oral administration.

8. The method according to claim 7, wherein the ammonium chloride, the sodium croscarmellose, the hydroxypropyl methylcellulose, and the magnesium stearate are comprised by microspheres, the microspheres enclosed by the enteric coating and providing a sustained release of the ammonium chloride.

9. The method according to claim 1, wherein the formulation is configured for external topical use and administering the formulation to the subject includes application of the formulation to subject's skin.

10. A method of treating a clinical manifestation of infection by a virus in a subject in need thereof, the method comprising:

administering a sustained release formulation to the subject, the sustained release formulation including a lysosomotropic agent including ammonium chloride, whereby the lysosomotropic agent interferes with viral uncoating, provides a viral-static effect, and allows immunological mechanisms of the subject to produce antibodies against the virus, wherein the virus includes SARS-CoV-2 virus;

monitoring the subject for at least one of alkalosis and acidosis, wherein the monitoring includes measuring a blood pH of the subject;

selectively adjusting the administering of the formulation to the subject based on the monitoring so that the subject is not exhibiting alkalosis and is not exhibiting acidosis, wherein the selectively adjusting includes adjusting the administering of the formulation to the subject until the blood pH of the subject is between about 7.35 and about 7.45; and continuing the administration of the formulation to the subject until an antibody to the virus is detected in the subject.

11. The method according to claim 10, wherein:

the sustained release formulation is configured in a unit dosage form; and the method further comprises measuring a blood pH of the subject and adjusting the administering of the sustained release formulation to the subject until the blood pH of the subject is between about 7.35 and about 7.45.

12. A method of treating a clinical manifestation of infection by a virus in a subject in need thereof, the method comprising:

administering a formulation to the subject, the formulation comprising ammonium chloride, at least one excipient, and an enteric coating configured for oral administration;

monitoring the subject for at least one of alkalosis and acidosis, wherein the monitoring includes measuring a blood pH of the subject;

selectively adjusting the administering of the formulation to the subject based on the monitoring so that the subject is not exhibiting alkalosis and is not exhibiting acidosis, wherein the selectively adjusting includes adjusting the administering of the formulation to the subject until the blood pH of the subject is between about 7.35 and about 7.45; and continuing the administration of the formulation to the subject until an antibody to the virus is detected in the subject.

13. The method of claim 12, wherein the formulation consists of the ammonium chloride, the at least one excipient, and the enteric coating.

14. The method of claim 12, wherein the formulation comprises microspheres consisting of the ammonium chloride and the at least one excipient, the microspheres contained within an enteric coated softgel or capsule, and the formulation is configured for sustained release.

15. The method of claim 1, wherein the formulation includes the enteric coating for oral administration, the enteric coating configured for sustained release of the lysosomotropic agent in the duodenum or upper tract of the intestine of the subject.

16. The method of claim 1, further including performing a polymerase chain reaction (PCR) test or reverse-transcription polymerase chain reaction (RT-PCR) test for viral genetic material and/or an antibody-based test for a viral antigen.

17. The method of claim 1, adjusting the formulation to mitigate the risk of gastric side effects.

18. The method of claim 1, further including a step of testing the subject for until a negative viral test is obtained.

19. The method of claim 1, wherein the formulation is configured to maintain a blood concentration of the lysosomotropic agent between a minimum effective concentration and a minimum toxic concentration.

* * * * *